United States Patent [19]

Strobel et al.

[11] Patent Number: 4,517,008

[45] Date of Patent: * May 14, 1985

[54] COMPOSITIONS CONTAINING AND METHODS OF USE OF AN INFECTIVITY-CURED HR PLASMID-BEARING MICROORGANISM

[75] Inventors: Gary A. Strobel; Andrea H. Gavlak; Jesse M. Jaynes, all of Bozeman, Mont.

[73] Assignee: Research and Development Institute, Inc. at Montana State University, Bozeman, Mont.

[ * ] Notice: The portion of the term of this patent subsequent to Jan. 10, 2001 has been disclaimed.

[21] Appl. No.: 389,070

[22] Filed: Jun. 16, 1982

Related U.S. Application Data

[63] Continuation-in-part of Ser. No. 260,167, May 4, 1981, Pat. No. 4,425,150.

[51] Int. Cl.$^3$ ............................................. A01N 63/00
[52] U.S. Cl. .................................. 71/77; 435/828; 71/79; 71/7; 47/57.6
[58] Field of Search ............... 71/65, 79, 77; 47/57.6; 435/828

[56] References Cited

U.S. PATENT DOCUMENTS

| | | | |
|---|---|---|---|
| 674,765 | 5/1901 | Hartleb et al. | 71/77 |
| 3,168,796 | 2/1965 | Scott et al. | 71/77 |
| 3,499,748 | 3/1970 | Fraser | 47/57.6 |
| 4,077,793 | 3/1978 | Krupika | 71/65 |
| 4,136,486 | 1/1979 | Franklin, Jr. et al. | 47/57.6 |
| 4,149,869 | 4/1979 | Lloyd | 47/57.6 |
| 4,425,150 | 1/1984 | Strobel et al. | |

OTHER PUBLICATIONS

C & E News, Dec. 8, 1980, p. 29.
Moore et al., Plasmid, vol. 8, pp. 617–628, (1979).
Stanek, Folia Microb., 21, pp. 213 et seq., (1976).
Chemical Abstracts, vol. 94, 1981, p. 188, Abstract No. 1868s.
Chemical Abstracts, vol. 78, 1973, p. 156, Abstract No. 53957j.
Chemical Abstracts, vol. 86, 1977, p. 259, Abstract No. 68086p.
Chemical Abstracts, vol. 92, 1980, p. 335, Abstract No. 194297v.

Primary Examiner—Catherine L. Mills
Attorney, Agent, or Firm—Lowe, King, Price & Becker

[57] ABSTRACT

A novel agriculturally useful composition that includes a seed treated with a selected infectivity-cured Hr plasmid-bearing microorganism. Also provided are methods of enhancing root elongation, shoot elongation or root development of selected seeds. These methods include treating a selected seed with the infectivity-cured Hr plasmid-bearing microorganism. In addition, there is provided a method of inducing germination of grass seed that involves treating a grass seed such as Kentucky bluegrass seed with a selected infectivity-cured Hr plasmid-bearing microorganism. Furthermore, there is provided a method of promoting plant growth at a lower soil temperature than is common at the time of planting a seed of the plant. Additionally, there is disclosed an inoculant for increasing nodulation, root mass and shoot mass in a leguminous plant. The inoculant contains a Rhizobium microorganism and a selected infectivity-cured Hr plasmid-bearing microorganism. Also, there is provided an agriculturally useful composition containing a suitable seed treated with this inoculant.

13 Claims, No Drawings

COMPOSITIONS CONTAINING AND METHODS OF USE OF AN INFECTIVITY-CURED HR PLASMID-BEARING MICROORGANISM

CROSS-REFERENCE TO RELATED APPLICATIONS

This application is a continuation-in-part of Ser. No. 260,167, filed May 4, 1981, now U.S. Pat. No. 4,425,150, issued Jan. 10, 1984.

TECHNICAL FIELD

This invention relates to the field of plant husbandry, and in particular relates to compositions containing and methods of use of an Hr plasmid-bearing microorganism free from pathogenicity to carrots.

BACKGROUND ART

It is known to improve seed germination, with this type of prior art being illustrated by U.S. Pat. No. 2,553,577 to Hale et al., and U.S. Pat. No. 2,690,388 to Hale. Treatment of a seed with a microorganism, particularly with a microorganism of the genus Rhizobium, is also known. This type of prior art is exemplified by U.S. Pat. No. 2,313,057 to Fischer, U.S. Pat. No. 3,168,796 to Scott et al, U.S. Pat. No. 3,499,748 to Fraser, U.S. Pat. No. 4,136,486 to Franklin, Jr. et al, U.S. Pat. No. 4,149,869 to Lloyd, and U.S. Pat. No. 4,161,397 to Bellet et al. In addition, U.S. Pat. No. 674,765 to Hartleb discloses a seed treated with a microorganism, states that nodule formation begins very shortly after the seed has become imbedded in the soil, and mentions rapid germination at lines 37 and 38 thereof. Furthermore, U.S. Pat. No. 4,077,793 to Krupicka discloses that treating seeds of certain crops such as maize, corn, potatoes and tomatoes with a biochemical material containing nitrogen-fixing soil microorganisms results in earlier germination, and reports unusually good yield. Also, *Chemical and Engineering News*, Dec. 8, 1980, p. 29 discusses the treatment of soybean seeds with nitrogen-fixing bacteria.

Additionally, it is known to stimulate the sprouting of cucumber and sugar beet plants by spreading a cell suspension of *Agrobacterium rhizogenes* on the surface of cucumber and sugar beet seeds. Illustrative of this type of prior art is M. Stanek, *Folia Microbiologica* 21(3):213 (1976). In this work, the microorganism was isolated from the surface of the hyphae of the fungus *Pythium debaryanum*. It is also disclosed in this work that treatment of the surface of sugar beet seeds with a suspension of the *A. rhizogenes* cells prevented black root disease, when the seeds were simultaneously artificially contaminated with the fungus *Phoma betae*.

Finally, the preparation of an infectivity-cured Hr plasmid-bearing microorganism is known. Illustrative of this prior art is Moore, Warren and Strobel, *Plasmid*, 2:617–626 (1979). This microorganism was prepared by treating *A. rhizogenes* $A_4$, which contains the Hr plasmid in nature, with ethidium bromide. This microorganism was free from pathogenicity to carrot. In this work, it is suggested in the paragraph bridging the two columns on p. 625 that induction of rooting may be a potential use of *A. rhizogenes* $A_4$. Induction of rooting is a potential use of pathogenic *A. rhizogenes* $A_4$ and is to be distinguished from either induction of germination (sprouting) or growth promoting activities such as the enhancement of root elongation, shoot elongation, and root development.

However, this and the other prior art of which we are aware, are deficient as failing to provide an agriculturally useful composition comprised of a seed treated with a selected infectivity-cured Hr plasmid-bearing microorganism. Furthermore, this art fails to provide methods of enhancing root elongation, shoot elongation or root development of a germinating seed that include treating a seed with a selected infectivity-cured Hr plasmid-bearing microorganism. Moreover, this prior art fails to provide a method of inducing germination of Kentucky bluegrass seed that involves treating the seed with a selected infectivity-cured Hr plasmid-bearing microorganism, and fails to provide a method of promoting plant growth at a lower soil temperature than is common at the time of planting a seed of the plant. Additionally, this prior art fails to provide an inoculant for increasing nodulation, root mass, and shoot mass in a leguminous plant, the inoculant containing a Rhizobium microorganism and a selected infectivity-cured Hr plasmid-bearing microorganism; and fails to provide an agriculaturally useful composition containing a suitable seed treated with this inoculant.

DISCLOSURE OF THE INVENTION

It is accordingly one object of the present invention to provide an agriculturally useful composition comprised of a seed treated with a selected infectivity-cured Hr plasmid-bearing microorganism.

A further object is to provide methods of enhancing root elongation, shoot elongation or root development of a germinating seed that includes treating a seed with a selected infectivity-cured Hr plasmid-bearing microorganism.

An even further object is to provide a method of inducing germination of a seed that involves treating the seed with a selected infectivity-cured Hr plasmid-bearing microorganism.

A still further object is to provide a method of promoting plant growth at a lower soil temperature than normally required when planting a seed of the plant.

An additional object is to provide an inoculant for increasing nodulation, root mass and shoot mass in a leguminous plant, the inoculant containing a Rhizobium microorganism and a selected infectivity-cured Hr plasmid-bearing microorganism.

An even additional object is to provide an agriculturally useful composition containing a suitable seed treated with this inoculant.

In satisfaction of the foregoing objects there is provided in its broadest aspect an infectivity-cured Hr plasmid-bearing microorganism free from pathogenicity to carrots and selected from the group consisting of (a) a microorganism type characterized by an induction of significantly enhanced shoot length in a germinating corn seed, when compared to *A. rhizogenes* $A_4$ ATCC 31799, and (b) a microorganism type characterized by significantly greater germination induction of Kentucky bluegrass seed, when compared to *A. rhizogenes* $A_4$ ATCC 31798.

In a further object of the invention there is provided an agriculturally useful composition comprising a seed of a vegetable or grain which has been treated with a composition of matter comprising an infectivity-cured Hr plasmid-bearing microorganism free from pathogenicity to carrots and selected from the group consisting of (a) a microorganism type characterized by an induction of significantly enhanced shoot length in a germinating corn seed, when compared to *A. rhizogenes* A₄ ATCC 31799, and (b) a microorganism type characterized by significantly greater germination induction of Kentucky bluegrass seed, when compared to *A. rhizogenes* A₄ ATCC 31798.

The seed may be pea, soybean, rice, grass such as Kentucky bluegrass, red fescue grass, winter rye or annular rye, corn, beans including pinto bean and green bean, wheat, e.g. Newana spring wheet, barley, e.g. shabet barley, sorghum, rice, cotton, broccoli, alfalfa, oats, sunflower, cabbage, tomatoes, watermelon, and lettuce.

In a further aspect of the invention, there is provided an agriculturally useful composition wherein the composition includes a seed of a vegetable or grain such as those selected from the group consisting of pea, soybean, grass such as Kentucky bluegrass, and rice treated with a selected infectivity-cured Hr plasmid-bearing microorganism. The microorganism is characterized by freedom from pathogenicity to carrots and significantly greater germination induction of Kentucky bluegrass seed, when compared to *A. rhizogenes* A₄ ATCC 31798.

In another embodiment, the compositions includes a seed of a vegetable or grain such as those selected from the group consisting of pea, soybean, corn, beans such as pinto bean, and rice treated with a selected infectivity-cured Hr plasmid-bearing microorganism. The microorganism is characterized by freedom from pathogenicity to carrots and an induction of significantly enhanced shoot length in a germinating corn seed, when compared to *A. rhizogenes* A₄ ATCC 31799.

In a second aspect of the invention, agriculturally useful methods are provided. In one embodiment, there is provided a method of enhancing root elongation of a germinating seed. In this method, a seed of a vegetable or grain selected from the group consisting of pea, wheet; barley, corn, sorghum and soybean is treated with a root elongation enhancing amount of a selected infectivity-cured Hr plasmid-bearing microorganism free from pathogenicity to carrots. The microorganism is either (1) a first microorganism type characterized by an induction of significantly enhanced shoot length in a germinating corn seed, when compared to *A. rhizogenes* A₄ ATCC 31799, or (2) a second microorganism type characterized by significantly greater germination induction of Kentucky bluegrass seed, when compared to *A. rhizogenes* A₄ ATCC 31798. However, when the seed is sorghum, the microorganism is the first microorganism type.

In another embodiment of this aspect of the invention, there is provided a method of enhancing root development of a germinating seed of a vegetable or grain. This method includes the step of treating a seed such as those selected from the group consisting of soybean, rice, bean, wheat, corn, pea and sorghum with a root development enhancing amount of a selected infectivity-cured Hr plasmid-bearing microorganism free from pathogenicity to carrots and that is either the first microorganism type or the second microorganism type. However, when the seed is sorghum, the microorganism is the first microorganism type.

In another embodiment of this aspect of the invention, there is provided a method of enhancing shoot elongation of a germinating seed of a vegetable or grain. This method includes treating a seed such as those selected from the group consisting of cotton, bean, rice, pea, wheat, barley, corn, rye grass, and broccoli, with a shoot elongation enhancing amount of a selected infectivity-cured Hr plasmid-bearing microorganism free from pathogenicity to carrots and that is either the first microorganism type or the second microorganism type. However, when the seed is corn or rye grass, the microorganism is the first microorganism type.

In a third aspect of the invention, there is provided a method of inducing germination of a grass such as Kentucky bluegrass seed. This method includes treating the seed with a germination inducing amount of a selected infectivity-cured Hr plasmid-bearing microorganism this is free from pathogenicity to carrots and that is the second microorganism type.

In a fourth aspect of the invention, there is provided a method of promoting plant growth at a lower soil temperature than is common at the time of planting a seed of the plant. The method includes the step of treating of seed such as soybean or corn seed with a selected infectivity-cured Hr plasmid-bearing microorganism that is free from pathogenicity to carrots and that is the second microorganism type.

In a further aspect of the present invention, there is provided an inoculant for increasing nodulation, root mass and shoot mass in a leguminous plant. The inoculant contains (a) a microorganism of the genus Rhizobium that is capable of inducing nodulation in the selected leguminous plant, and (b) a selected infectivity-cured Hr plasmid-bearing microorganism free from pathogenicity to carrots and that is either the first microorganism type or second microorganism type. The relative proportions of the Rhizobium microorganism and the plasmid-bearing microorganism are such that nodulation of a leguminous plant is increased as a consequence of treating a seed of the plant with a nodulation increasing amount of the inoculant.

Also provided is an agriculturally useful composition containing the inoculant and a seed of a leguminous plant in which the Rhizobium microorganism of the inoculant is capable of inducing nodulation. The inoculant is present in a nodulation increasing amount.

BEST MODE FOR CARRYING OUT THE INVENTION

As discussed, the present invention relates to compositions containing and methods of using a selected infectivity-cured Hr plasmid-bearing microorganism. By definition, for purposes of this document, an infectivity-cured Hr plasmid-bearing microorganism is free from pathogenicity to carrots and thus lacks the ability to induce root proliferation. In a preferred embodiment, the microorganism is an *A. rhizogenes* A₄ microorganism. For ease of understanding, much of the below discussion is specific to the *A. rhizogenes* A₄ microorganism, in which the Hr plasmid occurs in nature.

Broadly speaking, the infectivity-cured Hr plasmid-bearing microorganism is either a first microorganism type or is a second microorganism type. By a "first microorganism type" is meant a microorganism characterized by, for example, an induction of significantly enhanced shoot length in a germinating corn seed, when compared to *A. rhizogenes* A₄ ATCC 31799. This type is exemplified by *A. rhizogenes* A₄ ATCC 31798, and in this regard, reference is hereby made to the below Examples, which quantify other characteristics of this microorganism type. By a "second microorganism type" is meant a microorganism characterized by, for example, significantly greater germination induction of Kentucky bluegrass seed, when compared to *A. rhizogenes A₄ ATCC 31798. This type is exemplified by *A. rhizogenes* A₄ ATCC 31799, and in this regard, reference is hereby made to the below Examples, which quantify other characteristics of this microorganism type.

For the purposes of this invention, for the first microorganism type, experimentation identical to that used in obtaining the data in Table 5, is used to show the characteristic of significantly enhanced shoot length in comparison with the *A. rhizogenes* A₄ ATCC 31799 species. For the purposes of this invention, for the second microorganism type, experimentation identical to that used in obtaining the data in Table 10, is used to show the characteristic of significantly greater induction of Kentucky bluegrass seed in comparison with the *A. rhizogenes* A₄ ATCC 31798 species.

Preferred species useful in the invention are *A. rhizogenes* A₄ ATCC 31798 and *A. rhizogenes* A₄ ATCC 31799. A culture of each of these preferred species have been placed on deposit with the American Type Culture Collection, and the accession numbers set forth above have been assigned thereto. In each case, the deposit is restricted until such time as a patent has been issued disclosing the above deposits, except that access is available under 37 C.F.R. 1.14. After issuance of the patent, all restrictions on availability of the deposited cultures to the public will be irrevocably removed. The deposits will be maintained for a period of 30 years from the deposit date, and accordingly, the cultures will be permanently available to the public after issuance of the patent.

*A. rhizogenes* A₄ ATCC 31798 and *A. rhizogenes* A₄ ATCC 31799 were obtained by treating an *A. rhizogenes* A₄ wild strain with ethidium bromide according to the procedures of Lin and Kado, *Can. J. Microbiol.*, 23:1554–1561 (1977). The *A. rhizogenes* A₄ microorganism is a soil-inhabiting microorganism that was originally isolated by Dr. Peter Ark (University of California, Berkeley) from naturally infected roses exhibiting hairy root symptoms. The wild strain is known and available, and is described at p. 618 of the Moore, Warren and Strobel publication discussed earlier. The wild strain induces rooting of carrots, known as the "hairy root" syndrome, and is pathogenic to carrots. On carrot root disks inoculated with as few as 100 cells thereof, root proliferation is noted within two weeks. This microorganism causes root proliferation on members of many plant families including Leguminosiae and Compositae, and hence has a wide host range. As a result of this pathogenicity, it is better not to use the wild strain for agricultural purposes.

The preferred species were made by incorporating an about 100 micromolar amount of ethidum bromide into the nutrient-containing agar culture medium described below, and placing cells of the wild strain on the agar surface. After about six days, colonies were tested for the ability to induce root formation on carrot disks according to the carrot disk assay procedure on p. 618 of the Moore, Warren and Strobel publication. Those microorganisms that were found incapable of inducing root formation were further evaluated for growth promoting activities such as the enhancement of root elongation, shoot elongation, or root development (number of laterals, length of longest lateral, and/or adventitious root length), and for the capability to increase seed germination (sprouting). Testing of this type is discussed in detail in the below Examples. By this procedure, *A. rhizogenes* A₄ ATCC 31798 and *A. rhizogenes* A₄ ATCC 31799 were prepared and isolated. The preferred species are particularly characterized by freedom from pathogenicity to carrots, as shown by an inability to induce root proliferation in carrots.

By Tables 1 and 2 below, it is shown that the Hr plasmid controls the growth promoting activities mentioned above. This plasmid is correlated in the Moore, Warren and Strobel publication with the root proliferation infectivity of the *A. rhizogenes* A₄ wild strain. Thus, the Hr plasmid controls both growth promoting activities and infectivity. It is believed that, in addition, the Hr plasmid controls germination induction; promotes plant growth at a lower soil temperature than is common at the time of planting a seed of the plant; and functions to synergistically increase nodulation, root mass and shoot mass in a leguminous plant, when combined with a suitable Rhizobium microorganism.

The Hr plasmid is not found, in nature, in either *A. tumefaciens* or *A. radiobacter*. As demonstrated in Table 1, a seed treated with the *A. rhizogenes* A₄ wild strain or with either of the preferred species shows significant growth effects when compard to an untreated seed (control), whereas a seed treated with either *A. tumefaciens* or *A. radiobacter* does not show, on the whole, a significant growth effect. As demonstrated in Table 2, a seed treated with an *A. radiobacter* transconjugant that contains the Hr plasmid also shows significant growth effects, on the whole. Hence, these data show that the Hr plasmid is correlated with the growth promoting activities.

As a result of the ethidium bromide treatment described above, the infectivity gene was cured from the Hr plasmid in the case of the infectivity-cured Hr plasmid-bearing microorganism useful in the present invention. The *A. radiobacter* transconjugant was prepared by in vivo mating using known techniques, as a result of which the Hr plasmid was placed into this microorganism. Accordingly, it can be seen that the Hr plasmid could be placed into a microorganism other than *A. rhizogenes* A₄, and that the resulting microorganism could be treated with ethidium bromide to cure the infectivity gene from the Hr plasmid, and to produce a microorganism having an infectivity-cured Hr plasmid that is either the first microorganism type or the second microorganism type described above. As explained earlier, these microorganism types are illustrated by *A. rhizogenes* A₄ ATCC 31798 and *A. rhizogenes* A₄ ATCC 31799, respectively, and as can be appreciated from the below discussion and Examples, these species are believed to differ from each other in the composition of the infectivity-cured Hr plasmid. Hence, the present invention covers any microorganism that contains an infectivity-cured Hr plasmid that is functionally equivalent to either the infectivity-cured Hr plasmid in *A. rhizogenes* A₄ ATCC 31798 or the infectivity-cured Hr plasmid in *A. rhizogenes* A₄ ATCC 31799.

As a result of the ethidium bromide treatment, it has been unexpectedly discovered that the growth-promoting activities of the infectivity-cured Hr plasmid found in a microorganism in accordance with the invention are significantly enhanced, compared to the growth-promoting activities of a naturally occurring Hr plasmid, as found in the *A. rhizogenes* A₄ wild strain. As illustrated in the below Examples, the particular growth effect found to be enhanced varies according to the seed type, e.g., corn, pea or soybean, and varies acccording to whether the microorganism is the first or second microorganism type. In certain seeds such as wheat, especially in Newana spring wheat, a significant enhancement is not observed. However, as illustrated in the below Examples, in certain of these seeds, as well as in certain seeds in which significant enhancement is observed, it has been surprisingly discovered that the first and/or second microorganism types have a significant growth effect, compared to the same seed untreated with an *A. rhizogenes* A$_4$ microorganism (control of the Examples). In certain other species of seeds such as winter wheat, a significant growth effect of this type is not observed.

*A. rhizogenes* A$_4$ microorganisms can be easily cultured on medium containing the following nutrients per liter: 0.5 g KH$_2$PO$_4$, 10 g mannitol, 2 g L-glutamate, 0.2 g NaCl, 0.2 g MgSO$_4$, and 3.0 g yeast extract. An agar plate containing these nutrients is prepared by adjusting the pH of a solution containing these nutrients to 7.0, mixing 15 g/l of agar with the pH-adjusted solution, heating the resulting mixture, and pouring the hot liquid into a petri dish. The cells of *A. rhizogenes* A$_4$ grown either on plates or in liquid media are harvested as a paste from plates or by centrifugation from liquid media, frozen and then subjected to drying by lyophilization. The lyophilized cells possess biological activity at the same level as those that are freshly harvested.

In one embodiment of the agriculturally useful composition of the present invention, the microorganism-treated seed is pea seed, soybean seed, grass or rice. An especially preferred grass is Kentucky bluegrass seed (*Poa pratensis*). In this embodiment, the infectivity-cured Hr plasmid-bearing microorganism is the second microorganism type. In the case of pea, soybean or rice, significantly enhanced growth promoting effects are surprisingly observed when compared to the same seed treated with the *A. rhizogenes* A$_4$ wild strain. These effects are advantageous agriculturally as well as for land reclamation when the seed is a legume. The preferred species is *A. rhizogenes* A$_4$ ATCC 31799. Depending upon the seed selected, the growth promoting effect is enhanced shoot length and/or increased lateral root development. In the case of grass and especially Kentucky bluegrass, significantly enhanced germination is observed when compared to the same seed treated with the *A. rhizogenes* A$_4$ wild strain.

In another embodiment of the composition of the present invention, the microorganism treated seed is pea, soybean, corn, bean or rice, and the infectivity-cured Hr plasmid-bearing microorganism is the first microorganism type. Especially good results are obtained with pinto bean. In each instance, significantly enhanced growth promoting effects are surprisingly observed when compared to the same seed treated with the *A. rhizogenes* A$_4$ wild strain. These effects are advantageous agriculturally as well as for land reclamation when the seed is a legume. The preferred species is *A. rhizogenes* A$_4$ ATCC 31798. Depending upon the seed selected, the germinating seeds of this composition are characterized by enhanced root development (number of laterals, length of longest lateral and/or adventitious root length) and/or increased shoot length. As can be understood from the below Tables and as indicated by the above description, significantly enhanced effects are obtained when pea, soybean or rice is treated with either microorganism type, and especially with either preferred species.

In the agriculturally useful composition described above and in the methods described below, a selected seed is treated with an agriculturally efficacious amount of the infectivity-cured Hr plasmid-bearing microorganism according to the invention. Preferably, treatment of the seed is accomplished by coating the seed with cells of the microorganism.

In the case of *A. rhizogenes* A$_4$, the microorganism is grown for about three days at about room temperature on the culture medium described above, and the seed is coated by being placed directly into contact with the microorganism, which occurs in a slimy growth and thus readily adheres to the seed coat. Alternatively, lyophilized cells may be used to coat the seed by reconstituting the cells in water to about the same consistency as a fresh cell growth (paste), and then contacting the seed with the paste. The lyophilized cells possess biological activity at the same level as those that are freshly harvested. Either of these procedures is used in the Examples below.

Commercially, the coating procedures described above are not satisfactory since the microorganism-coated seed should be dry, although rice could be treated with a paste of reconstituted lyophilized cells. A commercially useful coating technique advantageously involves mixing an adherence-promoting additive such as kaolin or bentonite or freeze-dried cells of the microorganism, and then contacting the seed with the mixture. When kaolin is used as the additive, it is particularly suitable to combine about 3 parts of kaolin with about 1 part of cells (weight/weight). Alternatively, the seed could be first contacted with the adherence-promoting additive and then with the freeze-dried cells.

When the seed is coated by contacting the seed with the bacterial cells, or with the mixture of cells and adherence-promoting additive, the number of cells per seed depends upon factors such as the seed size and the relative amounts of the cells and of the additive. When a seed is simply contacted with a paste of *A rhizogenes* A$_4$ cells, about $10^9$–$10^{10}$ cells will be coated onto a relatively larger seed such as a soybean seed, and about $10^6$–$10^7$ cells will be coated onto a relatively smaller seed such as a grass seed. Optionally, there is added during the coating procedure a fungicide such as Captan ®. Experimentation has shown that either microorganism type may be compatible with a fungicide such as Captan ®. Other compatible additives could be included during the coating procedure.

In a second aspect of the present invention, agriculturally useful methods are provided. These methods include the step of treating a seed with an agriculturally efficacious amount of an infectivity-cured Hr plasmid-bearing microorganism that is either the first or second microorganism type. In this aspect of the invention, it is preferred that treatment of the seed be accomplished by coating the seed with cells of the microorganism. In this regard, the above description relating to coating a seed with the microorganism according to the invention is equally applicable to the agriculturally useful methods of the present invention.

In one embodiment of the agriculturally useful methods of the present invention, there is provided a method of enhancing root elongation of a germinating seed in which the agriculturally efficacious amount of the microorganism in accordance with the invention is more particularly a root elongation enhancing amount. The seed is pea, wheat, barley, corn, sorghum or soybean. However, when the seed is sorghum, the microorganism is the first microorganism type. Newana spring wheat and shabet barley are exemplary of these types. In each instance, a significantly enhanced root elongation is surprisingly observed in comparison with the same seed that is untreated with an *A. rhizogenes* A₄ microorganism (control of the Examples). An advantage of enhanced root elongation is that it promotes more rapid establishment of a plant in the soil.

In another embodiment, there is provided a method of enhancing root development of a germinating seed in which the agriculturally efficacious amount of the microorganism in accordance with the invention is more particularly a root development enhancing amount. Enhanced root development is characterized by an increase in the number of lateral roots, an increase in the length of the longest lateral root, and/or an increase in adventitious root length. The seed is soybean, rice, bean, pea, wheat or sorghum. Pinto bean and Newana spring wheat are exemplary of these types. However, when the seed is sorghum, the microorganism is the first microorganism type. In each instance, significantly enhanced root development is surprisingly observed in comparison with the same seed that is untreated with an *A. rhizogenes* A₄ microorganism (control of the Examples). When the seed is soybean or pea, the microorganism is preferably the second microorganism type, and when the seed is pinto bean or corn, the microorganism is preferably the first microorganism type. Enhanced root development is agriculturally advantageous because it facilitates a more rapid establishment of the plant in the soil and promotes passage of the plant through the early seedling stage at an accelerated rate and this reduces disease impact.

In still another embodiment, there is provided a method of enhancing shoot elongation of a germinating seed in which the agriculturally efficacious amount of the microorganism in accordance with the invention is more specifically a shoot elongation enhancing amount. The seed is cotton, bean, rice, pea, wheat, barley, corn, rye grass or broccoli. However, when the seed is corn or rye, the microorganism is the first microorganism type. Pinto bean, Newana spring wheat, shabet barley and winter rye are exemplary of those types. In each instance, significantly enhanced shoot elongation is surprisingly observed in comparison with the same seed that is untreated with an *A. rhizogenes* A₄ microorganism (control of the Examples). When the seed is rice, the microorganism is preferably the first microorganism type, and when the seed is barley, the microorganism is preferably the second microorganism type. An advantage of enhanced shoot elongation is that, for example, in the case of beans, the time for harvest may be reduced because of more rapid development of shoots and tops, and as a result early flowering. Enhanced shoot elongation is also advantageous in the case of rice since it results in the shoot extending above the water level more rapidly and thus reduces decay.

In a third aspect of the present invention, there is provided a method of inducting germination of grass seed, this aspect being exemplified by Kentucky bluegrass seed. Use of this method includes treating the seed with an agriculturally efficacious amount, more precisely a germination inducing amount, of the second microorganism type described above. Significantly enhanced germination is surprisingly observed when compared to the seed treated with the *A. rhizogenes* A₄ wild strain. The preferred species is *A. rhizogenes* A₄ ATCC 31799. It is preferred that treatment of the seed be accomplished by coating the seed with the microorganism. In this regard, the above disclosure relating to coating a seed with the microorganism in accordance with the invention is equally applicable to this aspect of the present invention.

In a fourth aspect of the present invention, there is provided a method of promoting plant growth at a lower soil temperature than is common at the time of planting a seed of the plant. This method has the advantage of permitting earlier planting, for example, at a soil temperature of about 58° F., rather than about 70° F. This method includes treating a corn or soybean seed with an agriculturally efficacious, more particularly a plant growth promoting, amount of the second microorganism type. Significantly enhanced root and shoot elongation are surprisingly observed for this microorganism type when compared to the same seed that is untreated with an *A. rhizogenes* A₄ microorganism. Enhancement is observed for the wild strain also. The preferred species is *A. rhizogenes* A₄ ATCC 31799, and it is preferred that the treatment be accomplished by coating the seed with the microorganism. In this regard, the above disclosure relating to coating a seed with the microorganism in accordance with the invention is equally applicable to this aspect of the invention.

Advantageously, the treated seed is incubated for at least about 1 to 2 days, at about room temperature, prior to being planted. Treatment of the seed with the microorganism is suitably also at about room temperature.

In a further aspect of the present invention, there is provided an inoculant for increasing nodulation, root mass and shoot mass in a leguminous plant. Increased nodulation has the advantage of increasing nitrogen fixation. The inoculant includes (a) a microorganism of the genus Rhizobium that is capable of inducing nodulation in the selected leguminous plant, and (b) an infectivity-cured Hr plasmid-bearing microorganism that is either the first or second microorganism type. Significantly increased nodulation, root mass and shoot mass are surprisingly observed with the wild strain when compared to treatment with *R. japonicum* only, and thus are believed to exist for the first and second microorganism types. The relative proportions of the Rhizobium microorganism and the first or second microorganism type in the inoculant are such that nodulation of a leguminous plant is increased as a result of treating a seed of the plant with a nodulation increasing amount of the inoculant. Suitably, at least about 1% of the total amount of the Rhizobium microorganism and of the first or second microorganism type in the inoculant, is the Rhizobium microorganism. Advantageously, the two microorganisms are present in substantially equal amounts in the inoculant. When the leguminous plant is a soybean plant, the Rhizobium microorganism is *Rhizobium japonicum*.

Also provided by the present invention is an agriculturally useful composition that includes this inoculant and a seed of a leguminous plant in which the Rhizobium microorganism of the inoculant is capable of inducing nodulation. The seed is treated with an agriculturally efficacious, more particularly a nodulation increasing, amount of the inoculant. Preferably, treatment of the seed is accomplished by coating the seed with cells of the inoculant. Any of the coating procedures described earlier may be used, with the commercially useful techniques being preferred. These procedures are, however, modified in that the Rhizobium microorganism is in each instance mixed with the infectivity-cured Hr plasmid-bearing microorganism prior to contacting a seed with cells of the Hr plasmid-bearing microorganism. One additional alternative coating procedure involves contacting a seed with finely chopped or ground peat containing cells of the mixture of the Rhizobium microorganism and the Hr plasmid-bearing microorganism. This procedure could be used in place of any of the earlier-described procedures. The number of cells coated onto each seed depends upon factors such as those discussed above.

Specific examples of the present invention will now be set forth. It is to be understood that these examples are merely illustrative, and are in no way to be interpreted as limiting the scope of the invention.

EXAMPLE 1

Ten to fifteen pea seeds are pretreated for five minutes in 5% sodium hypochlorite and then coated with cells of the *A. rhizogenes* A$_4$ wild strain in accordance with the coating procedure described above for the *A. rhizogenes* A$_4$ microorganism. Either fresh cells or reconstituted lyophilized cells are used. The coated cells are immediately placed on Steel Blue Anchor Seed Germination Blotter thoroughly moistened with water until free water no longer drips from its surface, and contained within an air-tight 15 cm × 15 cm × 3 cm plastic box. The box is incubated at 25° C. for 7 days, and the response of the germinating seeds is then evaluated.

This procedure is followed using cells of *A. rhizogenes* A$_4$ ATCC 31798, using cells of *A. rhizogenes* A$_4$ ATCC 31799, using cells of *A. tumefaciens,* and using cells of *A. radiobacter,* in place of cells of the wild strain. In addition, a control experiment is run in which this procedure is followed except that the seed is not treated with any microorganism.

Each experiment is carried out three times, and there is derived a value that represents an average of three replicates of 10–15 seeds, for each experiment. These values are set forth in Table 1.

EXAMPLE 2

Following the procedure of Example 1, using cells of an *A. radiobacter* transconjugant that contains the Hr plasmid, rather than using cells of the wild strain, and again carrying out a control experiment, the values set forth in Table 2 are obtained. Each of these values, and each of the values in Tables 3–9 and 11–14, represents an average of three replicates of 10–15 seeds.

EXAMPLE 3

Following the procedure of Example 1, except that the experimentation is limited to cells of the *A. rhizogenes* A$_4$ wild strain, cells of *A. rhizogenes* A$_4$ ATCC 31798, cells of *A. rhizogenes* A$_4$ ATCC 31799 and carrying out a control experiment, and except that soybean seed is substituted for pea seed, the results set forth in Table 3 and relating to the number of laterals and the length of the longest lateral are obtained.

Following the procedure of the previous paragraph, except that the period of incubation is 3 days, rather than 7 days, the results set forth in Table 3 and relating to root length are obtained.

TABLE 1

| Treatment Used | Response of Germinating Pea (*Pisum sativum*) - After 7 days* | | | |
|---|---|---|---|---|
| | Root Length (mm) | Shoot Length (mm) | Number of Laterals | Length of Longest Lateral (mm) |
| Control | 50.8$^y$ | 3.6$^z$ | 0.3$^x$ | 0.2$^z$ |
| Wild Strain | 70.4$^x$ | 7.8$^{yz}$ | 3.0$^y$ | 3.0$^{xy}$ |
| ATCC 31798 | 67.4$^x$ | 12.4$^{xy}$ | 5.3$^z$ | 4.2$^{xy}$ |
| ATCC 31799 | 71.6$^x$ | 13.5$^x$ | 5.6$^z$ | 5.2$^x$ |
| *A. tumefaciens* | 43.5$^y$ | 4.6$^z$ | 0.3$^x$ | 0.3$^z$ |
| *A. radiobacter* | 48.9$^y$ | 7.4$^{yz}$ | 0.07$^x$ | 0.02$^z$ |

*Differences were significant at the 1% level.
Numbers followed by the same letter(s) are in common statistically significant groups.

TABLE 2

| Treatment Used | Response of Germinating Pea (*Pisum sativum*) - After 7 days* | | | |
|---|---|---|---|---|
| | Root Length (mm) | Shoot Length[1] (mm) | Number of Laterals | Length of Longest Lateral[2] (mm) |
| Transconjugant | 76.3$^x$ | 32.1 | 7.4$^x$ | 13.7$^y$ |
| Control | 68.5$^x$ | 11.8 | 5.6$^x$ | 4.4$^x$ |

*Numbers followed by the same letter are in common statistically significant groups.
[1]Difference is significant at the 10% level.
[2]Differences are significant at the 5% level.

EXAMPLE 4

Following the procedure of the first paragraph of Example 3, except that shabet barley seed is substituted for soybean seed and the period of incubation is 5 days, rather than 7 days, the results set forth in Table 4 are obtained.

EXAMPLE 5

Following the procedure of Example 4, except that corn seed is substituted for barley seed and the period of incubation is 6 days, rather than 5 days, the results set forth in Table 5 are obtained.

EXAMPLE 6

Following the procedure of Example 4, except that rice seed is substituted for barley seed and the period of incubation is 8 days rather than 5 days, the results shown in Table 6 are obtained.

EXAMPLE 7

Following the procedure of Example 4, except that Newana spring wheat seed is substituted for barley seed, and the period of incubation is 3 days, rather than 5 days, the results set forth in Table 7 are obtained.

EXAMPLE 8

Following the procedure of Example 4, except that winter rye seed is substituted for barley seed and the period of incubation is 4 days, rather than 5 days, the results set forth in Table 8 are obtained.

EXAMPLE 9

Following the procedure of Example 4, except that sorghum seed is substituted for barley seed, and the period of incubation is 6 days, rather than 5 days, the results set forth in Table 9 are obtained.

TABLE 9

Response of Germinating Sorghum
(*Sorgum vulgare* var. *saccharatum*) -
After 6 Days*

| Treatment Used | Root Length[1] (mm) | Shoot Length[2] (mm) | Number of Laterals[3] | Length of Longest Lateral[3] (mm) |
|---|---|---|---|---|
| Control | 74.5$^x$ | 30.0 | 6.9 | 7.8 |
| Wild Strain | 93.5$^y$ | 43.5 | 3.0 | 4.0 |
| ATCC 31798 | 91.5$^y$ | 40.4 | 7.3 | 8.7 |
| ATCC 31799 | 75.7$^x$ | 41.7 | 6.6 | 6.3 |

*Numbers followed by the same letter are in common statistically significant groups.
[1]Differences were significant at the 1% level.
[2]Wild strain was statistically superior at 10% level when compared to the control.
[3]ATCC 31798 was statistically superior at 10% level, when compared to the control.

TABLE 10

| Treatment Used* | Percent of Kentucky Bluegrass (*Poa pratensis*) Germinating After 4 Days |
|---|---|
| Control | 8 |
| Wild Strain | 16 |
| ATCC 31798 | 15 |
| ATCC 31799 | 24 |

*Seed rot was significantly reduced on all seeds treated with the wild strain and the two mutants of *A. rhizogenes* A$_4$.

TABLE 11

Response of Germinating Cotton
(*Gossypium hirsutum*) - After 4 Days*

| Treatment Used | Root Length (mm) |
|---|---|
| Control | 31.8$^x$ |
| Wild Strain | 50.3$^y$ |
| ATCC 31798 | 45.8$^y$ |
| ATCC 31799 | 50.1$^y$ |

*Differences were significant at the 1% level.
Numbers followed by the same letter are in common statistically significant groups.

TABLE 12

Response of Germinating Cotton
(*Gossypium hirsutum*) - After 7 Days*

| Treatment Used | Root Length (mm) | Shoot Length (mm) |
|---|---|---|
| Control | 58.0$^x$ | 9.6$^x$ |
| Wild Strain | 56.4$^x$ | 11.2$^y$ |
| ATCC 31798 | 65.0$^x$ | 11.3$^y$ |
| ATCC 31799 | 56.1$^x$ | 11.8$^y$ |

*Differences were significant at the 5% level.
Numbers followed by the same letter are in common statistically significant groups.

EXAMPLE 13

Following the procedure of Example 4, except that pinto bean seed is substituted for barley seed, and the period of incubation is 7 days, rather than 5 days, the results set forth in Table 13 are obtained.

EXAMPLE 14

Following the procedure of Example 4, except that broccoli seed is substituted for barley seed and the period of incubation is 8 days, rather than 5 days, the results set forth in Table 14 are obtained.

EXAMPLE 15

Soybean seed is treated with cells of the *A. rhizogenes* A$_4$ wild strain in accordance with the procedure of Example 1. Each seed is deposited onto the surface of a 3'×4"×2" column of perlite. The seeds are watered every Monday, Wednesday and Friday with 500 ml of half-strength Hoaglands solution (Hoagland and Arnon, University of California, Agricultural Experiment Station Circular No. 347, 1938) minus all sources of nitrogen. After the seeds sprout, a suspension of *R. japonicum* is placed on the perlite surface next to each sprouting seed. The total number of *R. japonicum* cells per seed is about $10^8$. The plants are kept at 23°-25° C., and natural lighting is utilized under greenhouse conditions. After 5 weeks, the plants are removed, and the results set forth in Table 15 are obtained. Each value represents an average for 10 plants.

In order to provide a control, this procedure is followed except that the soybean seeds are not treated with the *A. rhizogenes* A$_4$ wild strain. Each value set forth in Table 15 for the control also represents an average for 10 plants.

TABLE 13

Response of Germinating Pinto Bean
(*Phaseolus vulgaris*) - After 7 Days*

| Treatment Used | Root Length (mm) | Shoot Length (mm) | Number of Laterals | Length of Longest Lateral (mm) |
|---|---|---|---|---|
| Control | 87.9$^x$ | 15.0$^x$ | 12.3$^x$ | 54.9$^x$ |
| Wild Strain | 91.0$^x$ | 30.2$^y$ | 17.2$^{xy}$ | 66.3$^x$ |
| ATCC 31798 | 114.1$^x$ | 29.4$^y$ | 20.7$^y$ | 69.4$^x$ |
| ATCC 31799 | 88.2$^x$ | 28.1$^y$ | 15.7$^{xy}$ | 76.6$^x$ |

*Differences were significant at the 5% level.
Numbers followed by the same letter(s) are in common statistically significant groups.

TABLE 14

Response of Germinating Broccoli
(*Brassica oleracea*) - After 8 Days*

| Treatment Used | Root Length (mm) | Shoot Length (mm) |
|---|---|---|
| Control | 66.3$^x$ | 61.4$^x$ |
| Wild Strain | 75.0$^x$ | 77.9$^y$ |
| ATCC 31798 | 76.6$^x$ | 72.8$^y$ |
| ATCC 31799 | 79.1$^x$ | 73.5$^y$ |

*Differences were significant at the 5% level.
Numbers followed by the same letter are in common statistically significant groups.

TABLE 15

Response of Germinating Soybean Seed

| Treatment Used | Number of Nodules[1] | Shoot Length[3] (mm) | Length of Longest Root (mm) | Root Mass[2] (g) | Shoot Mass[1] (g) | Nodule Mass[2] (g) |
|---|---|---|---|---|---|---|
| Control (treatment with *R. japonicum* only) | 12.8 | 158.5 | 245.8 | 0.06 | 0.17 | 0.087 |
| Wild Strain plus | 21.3 | 177.0 | 248.1 | 0.08 | 0.27 | 0.139 |

TABLE 3

Response of Germinating Soybean
(Glycine max)*

| Treatment Used | Root Length[1] (mm) | Number of Laterals[2] | Length of Longest Lateral[2] (mm) |
|---|---|---|---|
| Control | 16.9$^x$ | 11.8$^x$ | 9.5$^x$ |
| Wild Strain | 37.7$^y$ | 12.1$^x$ | 26.4$^y$ |
| ATCC 31798 | 40.3$^y$ | 17.7$^y$ | 27.0$^y$ |
| ATCC 31799 | 44.4$^y$ | 26.2$^y$ | 36.1$^z$ |

*Numbers followed by the same letter are in common statistically significant groups.
[1]Results after 3 days. Differences were significant at the 5% level.
[2]Results after 7 days. Differences were significant at the 1% level.

TABLE 4

Response of Germinating Shabet
Barley (Hordeum vulgare)
After 5 Days*

| Treatment Used | Root Length[1] (mm) | Shoot Length[2] (mm) | Number of Roots |
|---|---|---|---|
| Control | 67.5$^x$ | 21.8$^x$ | 5.6$^x$ |
| Wild Strain | 96.4$^y$ | 32.3$^y$ | 5.7$^x$ |
| ATCC 31798 | 90.1$^y$ | 29.7$^{xy}$ | 5.5$^x$ |
| ATCC 31799 | 97.0$^y$ | 35.0$^y$ | 6.0$^x$ |

*Numbers followed by the same letter(s) are in common statistically significant groups.
[1]Differences were significant at the 1% level.
[2]Differences were significant at the 5% level.

TABLE 5

Response of Germinating Corn
(Zea mays) - After 6 Days*

| Treatment Used | Root Length[1] (mm) | Shoot Length[2] (mm) | Number of Laterals[1] | Length of Longest Lateral[2] (mm) | Adventitious Root Length[2] (mm) |
|---|---|---|---|---|---|
| Control | 102.2$^x$ | 18.9$^x$ | 9.6$^x$ | 3.6$^x$ | 9.6$^y$ |
| Wild Strain | 129.1$^y$ | 28.4$^x$ | 21.7$^y$ | 8.6$^y$ | 21.3$^x$ |
| ATCC 31798 | 147.7$^y$ | 38.4$^y$ | 29.1$^z$ | 12.0$^y$ | 24.7$^x$ |
| ATCC 31799 | 142.7$^y$ | 28.5$^x$ | 23.9$^{yz}$ | 11.1$^y$ | 15.5$^{xy}$ |

*Numbers followed by the same letter(s) are in common statistically significant groups.
[1]Differences were significant at the 1% level.
[2]Differences were significant at the 5% level.

TABLE 6

Response of Germinating Rice
(Oryza sativa) - After 8 Days*

| Treatment Used | Root Length (mm) | Shoot Length[1] (mm) | Number of Laterals | Length of Longest Lateral[2] (mm) |
|---|---|---|---|---|
| Control | 52.7$^x$ | 12.5$^x$ | 47.9$^x$ | 14.0$^x$ |
| Wild Strain | 58.0$^x$ | 18.3$^{xy}$ | 62.9$^x$ | 22.8$^y$ |
| ATCC 31798 | 58.8$^x$ | 25.3$^z$ | 65.4$^x$ | 21.6$^y$ |
| ATCC 31799 | 62.4$^x$ | 20.0$^{yz}$ | 70.8$^x$ | 20.4$^y$ |

*Numbers followed by the same letter(s) are in common statistically significant groups.
[1]Differences were significant at the 5% level.
[2]Differences were significant at the 1% level.

TABLE 7

Response of Germinating Newana
Spring Wheat (Triticum aestivum) -
After 3 Days*

| Treatment Used | Root Length[1] (mm) | Shoot Length[2] (mm) | Number of Roots[2] |
|---|---|---|---|
| Control | 18.3$^x$ | 2.1$^x$ | 2.2$^x$ |
| Wild Strain | 28.4$^y$ | 4.6$^y$ | 2.9$^y$ |
| ATCC 31798 | 30.2$^y$ | 4.9$^y$ | 2.9$^y$ |
| ATCC 31799 | 28.4$^y$ | 4.3$^y$ | 2.8$^y$ |

*Numbers followed by the same letter are in common statistically significant groups.
[1]Differences were significant at the 1% level.
[2]Differences were significant at the 5% level.

TABLE 8

Response of Germinating Winter Rye
(Secalis cereale) - After 4 Days*

| Treatment Used | Root Length (mm) | Shoot Length[1] (mm) | Number of Roots |
|---|---|---|---|
| Control | 53.7$^x$ | 15.2 | 3.9$^x$ |
| Wild Strain | 58.8$^x$ | 18.6 | 4.3$^x$ |
| ATCC 31798 | 57.8$^x$ | 21.2 | 4.5$^x$ |
| ATCC 31799 | 58.4$^x$ | 17.8 | 3.9$^x$ |

*Numbers followed by the same letter are in common statistically significant groups.
[1]ATCC 31798 was statistically superior at the 10% level, when compared to the control.

EXAMPLE 10

The procedure of Example 4 is followed, except that Kentucky bluegrass seed is substituted for barley seed, except that the bluegrass seed is not pretreated with sodium hypochlorite, except that the period of incubation is 4 days, rather than 5 days, and except that 100 seeds per box, rather than 10–15 seeds per box are used. Each seed treated with an A. rhizogenes A$_4$ microorganism is coated with $10^6$–$10^7$ bacterial cells. The results set forth in Table 10 are obtained. Each of these values represents an average of three replicates of 100 seeds. As shown, ATCC 31799 produces significantly greater germination induction than ATCC 31798, and the wild strain produces substantially equivalent germination induction to that produced by ATCC 31798.

As indicated, Kentucky bluegrass seed rot is significantly reduced for seeds treated with the infectivity-cured Hr plasmid-bearing microorganism in accordance with the invention, as well as with the A. rhizogenes A$_4$ wild strain. Generally, seed rot is prevented by use of fungicides.

EXAMPLE 11

Following the procedure of Example 4, except that cotton seed is substituted for barley seed and the period of incubation is 4 days, rather than 5 days, the results set forth in Table 11 are obtained.

EXAMPLE 12

Following the procedure of Example 11, except that the period of incubation is 7 days, rather than 4 days, the results set forth in Table 12 are obtained.

TABLE 15-continued

| | Response of Germinating Soybean Seed | | | | | |
|---|---|---|---|---|---|---|
| Treatment Used | Number of Nodules[1] | Shoot Length[3] (mm) | Length of Longest Root (mm) | Root Mass[2] (g) | Shoot Mass[1] (g) | Nodule Mass[2] (g) |
| *R. japonicum* | | | | | | |

[1]Differences are significant at the 1% level using the analysis of variance statistical test.
[2]Differences are significant at the 5% level using the analysis of variance statistical test.
[3]Differences are significant at the 1% level using the student's T test, but are not significant using the analysis of variance statistical test.

In the case of the data set forth above for Newana spring wheat and barley, the significant differences shown in the Tables disappeared when the observations were made after a 7 day incubation period. However, the presence of the significant differences shown in the Tables for these seed types are nevertheless expected to be of importance. When the procedure of Example 4 was followed except that winter wheat seed was substituted for barley seed and the incubation period was seven days, no significant differences were observed.

APPLICABILITY

The invention provides enhanced growth promoting effects in sprouting seeds that are advantageous agriculturally, and that are advantageous for land reclamation when the seed is a legume. Furthermore, the invention helps establish lawns and sods by germination induction and increases nitrogen-fixation, root mass, shoot mass and nodule mass in legumes.

We claim:

1. A method for enhancing root elongation of a germinating seed selected from the group consisting of pea, wheat, barley, corn, sorghum and soybean, which method comprises treating said seed with a root elongation enhancing amount of an infectivity-cured Hr plasmid-bearing microorganism free from pathogenicity to carrots, said microorganism being an *A. rhizogenes* $A_4$ microorganism selected from the group consisting of (a) a first microorganism type characterized by an induction of significantly enhanced shoot length in a germinating corn seed, and having the characteristics of *A. rhizogenes* $A_4$ ATCC 31798, and (b) a second microorganism type characterized by significant germination induction of Kentucky bluegrass seed and having the characteristics of *A. rhizogenes* $A_4$ ATCC 31798.

2. A method according to claim 1 wherein said seed is coated with said microorganisms.

3. The method of claim 1, wherein said seed is selected from the group consisting of pea, Newana spring wheat, shabet barley, corn, sorghum, and soybean.

4. A method for enhancing root development of a germinating seed selected from the group consisting of soybean, rice, bean, pea, wheat, corn and sorghum, which comprises treating said seed with a root development enhancing amount of an infectivity-cured Hr plasmid-bearing *A. rhizogenes* $A_4$ microorganism free from pathogenicity to carrots and selected from the group consisting of (a) a first microorganism type characterized by an induction of significantly enhanced shoot length in a germinating corn seed, and having the characteristics of *A. rhizogenes* $A_4$ ATCC 31798, and (b) a second microorganism type characterized by significant germination induction of Kentucky bluegrass seed, and having the characteristics of *A. rhizogenes* ATCC 31799.

5. A method according to claim 4 wherein said seed is coated with said microorganisms.

6. The method of claim 4, wherein said microorganism is said second microorganism type, and said seed is soybean or pea.

7. The method of claim 4, wherein said microorganism is said first microorganism type, and said seed is pinto bean or corn.

8. The method of claim 4, wherein said seed is selected from the group consisting of soybean, rice, pinto bean, pea, Newana spring wheat, corn and sorghum.

9. A method of enhancing shoot elongation of a germinating seed selected from the group consisting of cotton, bean, rice, pea, wheat, barley, corn, rye grass and broccoli, which method comprises treating said seed with a shoot elongation enhancing amount of an infectivity-cured Hr plasmid-bearing $A_4$ microorganism free from pathogenicity to carrots and selected from the group consisting of (a) a first microorganism type characterized by an induction of significantly enhanced shoot length in a germinating corn seed, and having the characteristics of *A. rhizogenes* $A_4$ ATCC 31798, and (b) a second microorganism type characterized by significant germination induction of Kentucky bluegrass seed and having the characteristics of *A. rhizogenes* $A_4$ ATCC 31799.

10. A method according to claim 9 wherein said seed is coated with said microorganism.

11. The method of claim 9, wherein said microorganism is said first microorganism type, and said seed is rice.

12. The method of claim 9, wherein said microorganism is said second microorganism type, and said seed is shabet barley.

13. The method of claim 9, wherein said seed is selected from the group consisting of pinto bean, rice, pea, Newana spring wheat, shabet barley, corn, winter rye, and broccoli.

* * * * *

UNITED STATES PATENT AND TRADEMARK OFFICE
CERTIFICATE OF CORRECTION

PATENT NO. : 4,517,008
DATED : May 14, 1985
INVENTOR(S) : STROBEL et al

It is certified that error appears in the above-identified patent and that said Letters Patent is hereby corrected as shown below:

Under "APPLICABILITY": Col. 17; Claim 1; Line 44:

"ATCC 31798" should be --ATCC 31799--.

Col. 18; Claim 4, Line 17:

"ATCC 31798" should be --ATCC 31799--, and

Col. 18; Claim 4, Line 20:

"ATCC 31799" should be --ATCC 31798--.

Col. 18, Claim 9; Line 42:

"ATCC 31798" should be --ATCC 31799--, and

Col. 18, Claim 9; Line 46:

"ATCC 31799" should be --ATCC 31798--.

Signed and Sealed this

Twenty-first Day of January 1986

[SEAL]

Attest:

DONALD J. QUIGG

Attesting Officer     Commissioner of Patents and Trademarks